United States Patent [19]

Rupp et al.

[11] Patent Number: 5,693,066

[45] Date of Patent: Dec. 2, 1997

[54] STENT MOUNTING AND TRANSFER DEVICE AND METHOD

[75] Inventors: Garry Eugene Rupp, Santee; James M. Shy, Chula Vista; Cecilia Chao, Vista; Kazuo Sasamine, Lemon Grove, all of Calif.

[73] Assignee: Medtronic, Inc., Minneapolis, Minn.

[21] Appl. No.: 576,720

[22] Filed: Dec. 21, 1995

[51] Int. Cl.⁶ .................................................. A61M 29/00
[52] U.S. Cl. ............................. 606/198; 623/1; 623/12
[58] Field of Search ........................... 606/1, 108, 191, 606/192, 194, 195, 198; 604/96; 128/898, 899; 623/1, 12

[56] References Cited

U.S. PATENT DOCUMENTS

| 5,026,377 | 6/1991 | Burton et al. |
| 5,041,126 | 8/1991 | Gianturco ................... 623/1 |
| 5,108,416 | 4/1992 | Ryan et al. |
| 5,158,548 | 10/1992 | Lau et al. |
| 5,183,085 | 2/1993 | Timmermans ............... 623/1 |
| 5,190,058 | 3/1993 | Jones et al. |
| 5,192,297 | 3/1993 | Hull. |
| 5,201,757 | 4/1993 | Heyn et al. |
| 5,226,889 | 7/1993 | Sheiban. |
| 5,226,913 | 7/1993 | Pinchuk ....................... 623/1 |
| 5,242,399 | 9/1993 | Lau et al. |
| 5,266,073 | 11/1993 | Wall. |
| 5,306,294 | 4/1994 | Winston et al. |
| 5,338,296 | 8/1994 | Dalessandro et al. |
| 5,344,426 | 9/1994 | Lau et al. |
| 5,360,401 | 11/1994 | Turnland. |
| 5,368,566 | 11/1994 | Crocker. |
| 5,387,235 | 2/1995 | Chuter. |
| 5,391,172 | 2/1995 | Williams et al. |

*Primary Examiner*—William Lewis
*Attorney, Agent, or Firm*—John R. Duncan; Dianne M. F. Plunkett; Harold R. Patton

[57] ABSTRACT

A mounting and transfer device and method for installing a stent on a delivery device that inserts the stent into a body lumen. The device includes a generally cylindrical mandrel for receiving and frictionally holding a stent, a handle at a first end of the mandrel and a guide rod extending axially from the second of the mandrel. The second end of the mandrel has a conical recess surrounding the guide rod exit. In use, a stent is placed on the mandrel, the distal end of the guide rod is fully inserted into a guide wire lumen at an end a delivery system such as a catheter and the stent is slid from the mandrel onto the balloon and crimped in place. A tube of heat shrinkable material may be placed over the stent on the mandrel and heat shrunk to lightly press against the stent. The tube and stent are transferred to the balloon and crimped. The tube protects the stent against damage during transfer and crimping and is easily removed thereafter since crimping reduces the outside diameter of the stent to less than the internal diameter of the tube.

16 Claims, 2 Drawing Sheets 5,693,066

STENT MOUNTING AND TRANSFER DEVICE AND METHOD

FIELD OF THE INVENTION

This invention relates in general to intervascular stent implants for maintaining vascular patency in humans and animals and more particularly to a method and apparatus for supporting a stent and for transferring the stent to a delivery system such as a balloon catheter.

BACKGROUND OF THE INVENTION

Percutaneous transluminal coronary angioplasty (PTCA) is used to reduce arterial build-up of cholesterol fats or atherosclerotic plaque. Typically a guidewire is steered through the vascular system to the site of therapy. A guiding catheter, for example, can then be advanced over the guidewire and a balloon catheter advanced within the guiding catheter over the guidewire. The balloon at the distal end of the catheter is inflated causing the site of the stenosis to widen. The dilatation of the occlusion, however, can form flaps, fissures and dissections which threaten re-closure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. Reducing the possibility of restenosis after angioplasty reduces the likelihood that a secondary angioplasty procedure or a surgical bypass operation will be necessary.

An implanted prosthesis such as a stent can preclude additional procedures and maintain vascular patency by mechanically supporting dilated vessels to prevent vessel collapse. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in size from 1.5 mm in the coronary vessels to 30 mm in the aortic vessel. The invention applies to acute and chronic closure or reclosure of body lumens.

A stent typically is a cylindrically shaped device formed from wire(s) or a tube and intended to act as a permanent prosthesis. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable. A plastically deformable stent can be implanted during a single angioplasty procedure by using a balloon catheter bearing a stent which has been crimped onto the balloon. Stents radially expand as the balloon is inflated, forcing the stent into contact with the body lumen thereby forming a supporting relationship with the vessel walls. Deployment is effected after the stent has been introduced percutaneously, transported transluminally and positioned at a desired location by means of the balloon catheter.

The stainless-steel or tantalum mesh stent that props open blocked coronary arteries, keeps them from reclosing after balloon angioplasty. A balloon of appropriate size and pressure is first used to open the lesion. The process is repeated with a stent crimped on a balloon. The stent is deployed when the balloon is inflated. The stent remains as a permanent scaffold after the balloon is withdrawn. A high pressure balloon may be preferable for stent deployment because the stent must be forced against the artery's interior wall so that it will fully expand thereby precluding the ends of the stent from hanging down into the channel encouraging the formation of thrombus.

A number of different stent structures and placement instruments have been developed. For example, Wall in U.S. Pat. No. 5,266,073 describes a rolled tubular stent carried at the end of a tubular catheter with a second catheter threaded therethrough to carry a balloon. The assembly is inserted into an artery until the stent is at the proper location, then the balloon catheter is positioned within the stent and expanded to expand, unroll and lock the stent. This arrangement usually requires an undesirably large diameter catheter for carrying the stent and includes a complex and possibly unreliable locking method for holding the stent in the expanded position. Also, non-uniform stent expansion may occur, since the expanding balloon cannot directly contact the portion of the stent that overlaps its carrier catheter.

Other stent delivery systems have a self-expanding stent compressed in a tube, such as that described by Burton et al. in U.S. Pat. No. 5,026,377. The tube is inserted until the stent is in the desired location and the stent is forced from the tube and expands into contact with the vessel wall. A balloon catheter may be inserted and expanded to further expand the stent. Problems may arise with maintaining the partially expanded stent in position and preventing pushing the stent out of position during insertion of the balloon catheter.

Others have used a rolled tubular stent placed around a balloon catheter and covered by a tubular sheath connected to a guidewire extending through the catheter, such as is described by Lau et al. in U.S. Pat. No. 5,158,548. The assembly is inserted into a desired location in a body lumen, the sheath is moved longitudinally by the guidewire away from the stent and the balloon is expanded to expand the stent. This requires a complex tubular catheter, sheath and stent assembly.

Balloon catheters are available with a stent preloaded around the balloon. This requires a second balloon catheter to be used to dilate the lesion enough to allow the stent to enter. Subsequently, the catheter bearing the stent is introduced and the stent emplaced. This requires the use of two expensive catheters to complete placement of the stent and catheterization.

Loose stents are available which users simply slip over a balloon catheter and crimp against the catheter balloon with the fingers. While this arrangement is simple and quick, the stent may be damaged during storage and handling prior to use, while it is being placed over the catheter balloon or during the crimping step. Damaged stents cannot be used. If damage to the stent is not noticed, the stent may not perform as intended in use. Further, depending on the type of delivery system fitting the stent over the delivery end without damage is sometimes difficult.

Thus, there is a continuing need for improved devices and methods for mounting a stent onto a delivery system such as a balloon catheter that are simpler, less expensive, more convenient, more reliable and avoid damage to the stent.

SUMMARY OF THE INVENTION

The above-noted problems, and others, are overcome in accordance with this invention by a stent storage, mounting and transfer device and method comprising a generally cylindrical mandrel sized to frictionally hold a stent thereon, having a handle at one end for manipulating the device and a guide rod extending substantially coaxially from the other end of the mandrel. A recess is preferably provided in the guide rod end of the mandrel.

To transfer a stent from the device to a balloon, the guide rod is inserted into a guide wire lumen at the end of a delivery system until the end of the balloon enters the mandrel recess. The stent then is slid from the mandrel onto the balloon. The guide rod is removed from the guide wire lumen and the stent is crimped in place, either manually or using a conventional crimping device.

Preferably, the wrapped balloon has a diameter slightly less than the mandrel diameter. While for best results the handle means comprises an enlarged, elongated knob-like end for easy grasping, a simple continuation of the mandrel, with or without a roughened or knurled surface, could be used if desired.

In order to provide protection to the stent during the transfer from mandrel to balloon and during the crimping step, preferably a thin tubular membrane of heat shrinkable material is placed over the stent on the mandrel and heated to shrink the tube against the stent. Only light pressure is required to provide optimum support to the stent during transfer and crimping. After crimping the stent has a smaller diameter than the membrane, so the membrane is no longer in contact with the stent and can be easily removed.

A stent may be mounted on the mandrel just before transfer to a catheter balloon if desired. Alternately, stents, in particular with the sheath of heat shrunk tubing, may be assembled in a factory environment and shipped to users for quick and easy transfer to balloons.

It is, therefore, an object of this invention to provide a device and method for placing stents onto any of a variety of delivery systems. Another object of the invention is to reduce or prevent damage to stents during placement onto delivery systems. A further object is to provide a removable protective sheath for a stent during stent placement onto a delivery system. Yet another object is to provide an arrangement in which a single balloon catheter can be used to dilate a lesion and place a stent at the lesion site. Other objects and advantages of the transfer device and method of this invention will become apparent upon reading the following description of preferred embodiments.

BRIEF DESCRIPTION OF THE DRAWING

Details of the invention, and of preferred embodiments thereof, will be further understood upon reference to the drawing, wherein.

DETAILED DESCRIPTION OF PREFERRED EMBODIMENTS

Figure 1:
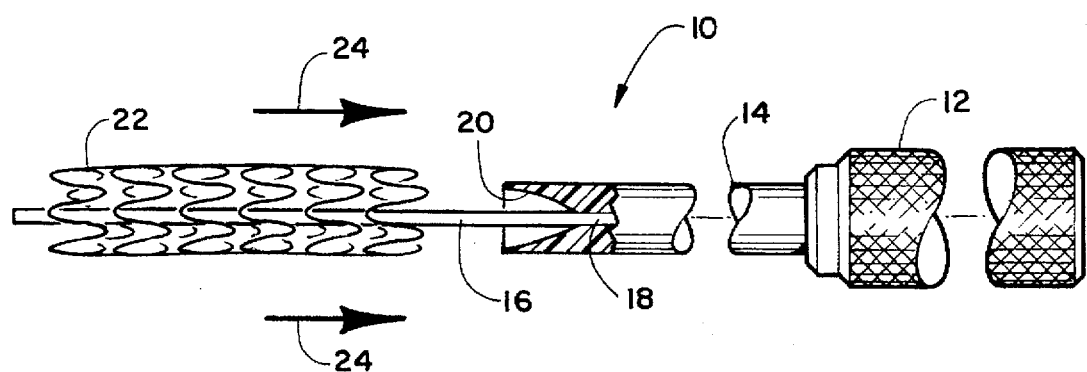
FIG. 1 is a side elevation view of the transfer device of this invention, partially cut away, during loading of a stent thereon and showing the end recess.

Referring to FIG. 1, there is seen a stent storage and delivery device 10 made up of a handle 12, a mandrel 14 and a guide rod 16. Handle 12 may have any suitable configuration for ease of manipulation of transfer device 10. An elongated handle having sufficient diameter for convenient manipulation and having a knurled or otherwise roughened surface is preferred. Typically, handle 12 may have a length of about 1.5 in. and a diameter of about 0.5 in. However, if desired other handled configurations, such as a short knob could be used. If desired, for simplicity, the handle portion could simply be a continuation of mandrel 14, preferably roughened for ease of griping.

Mandrel 14 is generally cylindrical and has any suitable length. The diameter of mandrel 14 would be equal to, or greater than, the diameter of the balloon onto which a stent is to be transferred, as detailed below. Typically, mandrel 14 may have a length of about 1.6 in. and a diameter of about 0.05 in.

Mandrel 14 and handle 12 may be formed from any suitable material. Preferably, for lowest cost and ease of manufacture, they are formed from a suitable thermoplastic or thermoset plastic by injection molding. Typically, handle 12 and mandrel 14 are formed from a resin selected from the group consisting of acetal, polycarbonate, polyamide, or any engineering resins suitable to the application. If desired, the mandrel and handle could be manufactured separately and bonded together or could be machined from a metal, such as aluminum.

Guide rod 16 extends from the distal end of mandrel 14 and is preferably coaxial with mandrel 14. Any suitable material may be used for guide rod 16, including metals, high stiffness plastics, metals coated with resins or coatings that reduce the coefficient of friction on the guide rod and the like. For optimum results, stainless steel, or fluoroplastic resin coated metal are preferred. Guide rod 16 is secured into an axial hole 18 in mandrel 14, as seen in the cut away end of mandrel 14. Hole 18 can be formed during injection molding of the mandrel or could be drilled in a conventional manner. The diameter of guide rod 16 preferably is a slip fit into the delivery system central channel and is secured into hole 18 with an adhesive or by press fitting into a slightly undersize hole. Typically, guide rod 16 has an overall length of about 2 in., with about 0.2 in. inserted into hole 18 and has a diameter of about 0.015 in. For a press fit, this guide rod 16 would preferably be used with a 0.0145 in. diameter hole. The ends of guide rod 16 are preferably rounded for ease of insertion of the proximal end into mandrel 14 and of the distal end into a delivery system orifice.

The distal end of mandrel 14 preferably has a recess 20 for receiving an end of a wrapped balloon at the end of the stent delivery system, as detailed below. Recess 20 is preferably generally conical, typically having a depth of about 0.06 inches to 0.25 inches and a base diameter of about 0.045 in.

Figure 2:
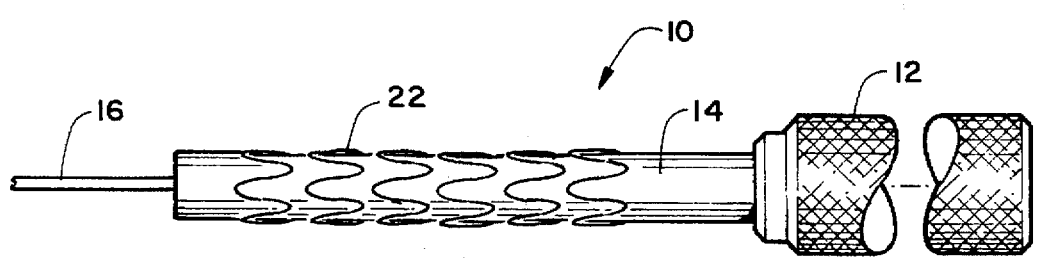
FIG. 2 is a side elevation view of the transfer device with a stent in place.

A stent 22 is installed by slipping the stent over guide rod 16 and mandrel 14, to the position shown in FIG. 2. Preferably, stent 22 is a light friction fit onto mandrel 14. Since stents are generally flexible and elastic, a very slight expansion as a stent 22 is slipped over mandrel 14 will provide sufficient friction to hold the stent in place. Excessive stretching of stent 22 during installation should be avoided to prevent distortion or damage to the stent. The mandrel preferably is be manufactured with a slight gradient that increases from the handle to guide rod. The diameter gradient ranges from about 2 to 10%. This will assist in keeping the stent from sliding off the mandrel section.

Any suitable stent may be used. The transfer device of this invention is particularly useful with the Wiktor coronary stent, available from Medtronic, Inc., Minneapolis, Minn.

Stent 22 can be made of any suitable inert, biocompatible-material with high corrosion resistance that can be plastically deformed at low to moderate stress levels such as tantalum, the preferred embodiment. Other acceptable materials include nickel titanium, stainless steel, titanium ASTM F63–83 Grade 1, niobium or high carat gold K 19–22.

Figure 3:
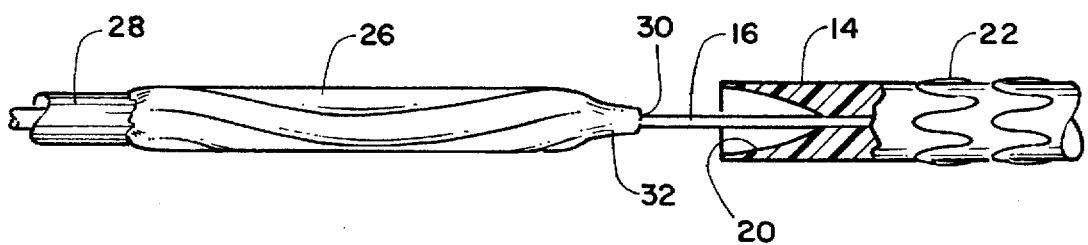
FIG. 3 is a side elevation view, partially cut away, showing alignment of a delivery system balloon with the transfer device.
Figure 4:
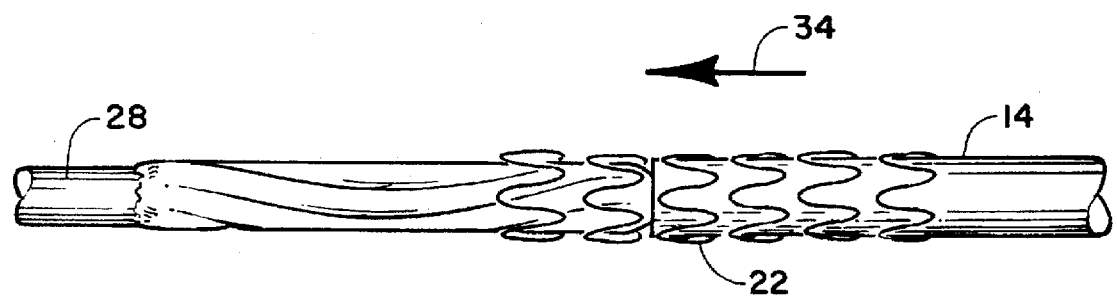
FIG. 4 is a side elevation view of the transfer device and balloon showing transfer of the stent to the balloon.

As seen in FIG. 3, transfer of stent 22 to a wrapped balloon 26 at the end of a catheter 28 (or other delivery system) is begun by inserting guide rod 16 into orifice 30 through balloon 26. When guide rod 16 is fully inserted, tapered end 32 will enter recess 20 in mandrel 14 so that there is no significant gap between the outer surface of the mandrel and the outer surface of balloon 26 as seen in FIG. 4. Then stent 22 is slid in the direction of arrow 34 from mandrel 14 onto balloon 26 as shown in progress in FIG. 4. Since the diameter of balloon 26 is no larger than that of mandrel 14 and preferably somewhat smaller, stent 22 will be fairly loose on the balloon.

Figure 5:
FIG. 5 is a side elevation view of the delivery system with the stent crimped over the balloon.

After stent 22 is fully transferred to balloon 26, transfer device 10 is removed and the stent is crimped against the balloon, either manually with finger pressure or with a conventional crimping tool (not shown). As seen in FIG. 5, stent 22 is in tight, resilient contact with balloon 26 and is ready for use. Stent 22 will stay with the balloon as catheter 28 and the stent/balloon assembly is inserted into a body lumen.

Figure 6:
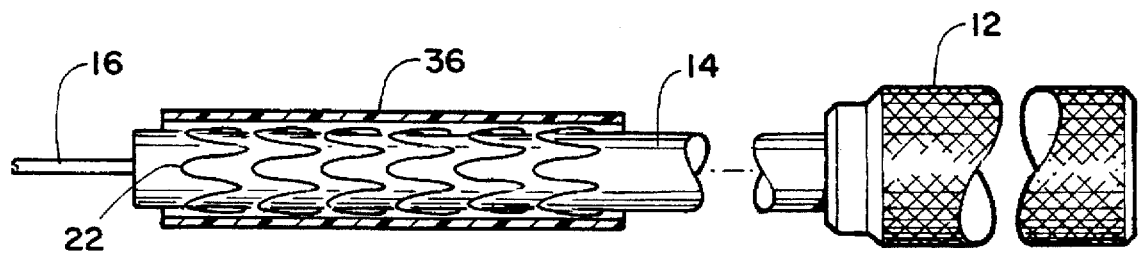
FIG. 6 is a side elevation view, partially cut away, showing an alternate embodiment including a stent sheath.

A further embodiment of the stent transfer device is shown in FIG. 6. Here, handle 12, mandrel 14 and guide rod 16 are as described above. A suitable stent 22 is installed on mandrel 14 in the same manner as earlier described. In this embodiment, a thin tube 36 of heat shrinkable material, such as fluoroplastic, polyethylene, polyamide or other heat shrinkable engineering resin is loosely placed over stent. Tube 36 is heated, such as with hot air, a heating block or high powered light to shrink the tube into light pressure contact with stent 22. While stent 22 is being transferred to a catheter balloon 26, tube 36 will reinforce the stent and prevent damage or distortion of the stent by allowing uniform compression. Stent 22 can be crimped with tube 36 in place, protecting the stent against damage during crimping. When stent 22 is fully crimped, the diameter of the stent will be reduced so that tube 36 can be easily slipped off and the system configuration will be as shown in FIG. 5.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

We claim:

1. A combination stent and stent mounting and transfer device which comprises:
    a generally cylindrical mandrel having a diameter sized to receive a stent of predetermined diameter and frictionally retain said stent thereon;
    handle means at a proximal end of said mandrel;
    guide means extending from approximately the center of a distal end of said mandrel and extending substantially coaxial therewith; and
    a recess in said distal end of said mandrel;
    whereby a stent may be installed on said mandrel, said guide means may be inserted into a guide wire lumen at a catheter end until said balloon contacts said recess and said stent can be slid from said mandrel onto said balloon.

2. The stent mounting and transfer device according to claim 1 further including a length of heat shrinkable tubing over said stent on said mandrel for heating to shrink said tubing over said stent.

3. The stent mounting and transfer device according to claim 1 wherein said handle and said mandrel are formed as a single unit from a material selected from the group consisting of acetal, polyamide and polycarbonate resins.

4. The stent mounting and transfer device according to claim 1 wherein said mandrel diameter gradient ranges from about 2 to 10% from said handle to said guide wire.

5. The stent mounting and transfer device according to claim 1 wherein said guide means is rod formed from a material selected from the group consisting of stainless steel or a fluoroplastic resin coated metal.

6. A combination stent and storage and transfer device which comprises:
    a generally cylindrical mandrel having a predetermined outside diameter;
    handle means at a proximal end of said mandrel;
    guide means extending from a distal end of said mandrel, substantially coaxial with said mandrel and adapted to receive a delivery system tubular balloon thereover;
    a expandable tubular stent on said mandrel, said stent having an inside diameter such as to frictionally retain said stent on said mandrel; and
    tubular means over said stent and pressing said stent against said mandrel;
    whereby said stent can be slidingly moved along said mandrel and onto a delivery system tubular balloon on said guide means and in contact with said mandrel second end.

7. The stent storage and transfer device according to claim 6, further including a conical, axial recess in said mandrel second end for receiving an end of a tubular balloon on said guide means.

8. The stent storage and transfer device according to claim 6, wherein said guide means is an elongated metal rod having a predetermined diameter adapted to slidingly fit within a predetermined tubular balloon inside diameter.

9. The stent storage and transfer device according to claim 8 wherein said guide rod is formed from a material selected from the group consisting of stainless steel and fluoroplastic resin coated metal.

10. The stent storage and transfer device according to claim 6 wherein said handle and said mandrel are formed as a single unit from a material selected from the group consisting of acetal, polyamide and polycarbonate resins.

11. The stent storage and transfer device according to claim 6 wherein said tubular means comprises a tube of heat shrinkable material that has been heated to shrink against said stent.

12. A method for mounting a stent onto a delivery system balloon which comprises the steps of:
    sliding a stent onto an end of a mandrel sized to frictionally hold said stent in place;

sliding tubular balloon, carried by a delivery means, onto a guide rod extending from said mandrel end until said tubular balloon contacts said mandrel end;

sliding said stent from said mandrel onto said tubular balloon;

removing said mandrel and guide rod; and crimping said stent onto said balloon.

13. The method according to claim 12 further including the steps of placing a tube of heat shrinkable tubing over said stent on said mandrel prior to slipping said stent onto said balloon and heating said tube to shrink said tube over said stent.

14. The method according to claim 13 wherein said heat shrinkable material is selected from the group consisting of heat shrinkable fluoroplastic, polyamide and polyethylene resins.

15. The method according to claim 12 wherein said crimping is accomplished by finger pressure.

16. The method according to claim 12 wherein said mandrel end is recessed and said balloon is brought into contact with said mandrel end by pressing a distal end of said balloon into said recess.

* * * * *